(12) United States Patent
Dabre et al.

(10) Patent No.: US 8,821,924 B2
(45) Date of Patent: Sep. 2, 2014

(54) RHEIN OR DIACEREIN COMPOSITIONS

(75) Inventors: Rahul Dabre, Nagpur (IN); Girish Kumar Jain, Delhi (IN); Cyril Estanove, Chavenay (FR); François Pruvost, Quimper (FR); Marie Francoise Pruvost, legal representatives, Nantes (FR); Roshanlal Sandal, Ferozpur (IN); Prashant Mandaogade, Amrarati (IN); Premchand Nakhat, Yawatmal (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 953 days.

(21) Appl. No.: 12/677,532

(22) PCT Filed: Sep. 13, 2008
(Under 37 CFR 1.47)

(86) PCT No.: PCT/IB2008/053716
§ 371 (c)(1),
(2), (4) Date: Sep. 20, 2011

(87) PCT Pub. No.: WO2009/034558
PCT Pub. Date: Mar. 19, 2009

(65) Prior Publication Data
US 2012/0070492 A1    Mar. 22, 2012

(30) Foreign Application Priority Data

Sep. 14, 2007 (IN) .......... 1766/MUM/2007
Sep. 27, 2007 (IN) .......... 1896/MUM/2007
Sep. 27, 2007 (IN) .......... 1897/MUM/2007

(51) Int. Cl.
*A61K 9/48* (2006.01)

(52) U.S. Cl.
USPC .......................................... 424/451

(58) Field of Classification Search
None
See application file for complete search history.

(56) References Cited

U.S. PATENT DOCUMENTS

| 5,449,521 A | * | 9/1995 | Lovrecich | .......... 424/489 |
| 5,952,383 A | * | 9/1999 | Metziger et al. | .......... 514/569 |
| 6,124,358 A | | 9/2000 | Estanove et al. | |
| 2006/0286162 A1 | * | 12/2006 | Glanzer | .......... 424/451 |

FOREIGN PATENT DOCUMENTS

EP    0371431 A    6/1990

* cited by examiner

*Primary Examiner* — Snigdha Maewall
(74) *Attorney, Agent, or Firm* — Bio Intellectual Property Services LLC (Bio IPS); O. (Sam) Zaghmout (57) ABSTRACT

The invention relates to pharmaceutical compositions comprising rhein or diacerein or salts or esters or prodrugs thereof, optionally with one or more pharmaceutically acceptable excipients. The invention also relates to the methods for preparing such compositions.

6 Claims, 3 Drawing Sheets

FIGURE 1: X-ray diffraction pattern of Composition of the present invention

FIGURE 2: X-ray diffraction pattern of plain Diacerein

FIGURE 3: Comparative dissolution data of Art 50® and composition of the present invention (Example –7, 8, 9 and 10)

RHEIN OR DIACEREIN COMPOSITIONS

FIELD OF THE INVENTION

The invention relates to pharmaceutical compositions comprising rhein or diacerein or salts or esters or prodrugs thereof, optionally with one or more pharmaceutically acceptable excipients. The invention also relates to methods for preparing such compositions.

BACKGROUND OF THE INVENTION

Chemically, rhein is 9,10-dihydro-4,5-dihydroxy-9,10-dioxo-2-anthracene carboxylic acid having a structure of Formula I and diacerein is 4,5-bis(acetyloxy)9,10-dihydro-4,5-dihydroxy-9,10-dioxo-2-anthracenecarboxylic acid having a structure of Formula II. Diacerein is widely used in the treatment of osteoarthritis and has a unique mode of action that differentiates it from non-steroidal anti-inflammatory drugs (NSAIDs) and other conventional forms of drug therapy. Presently, diacerein capsules are available in 50 mg strength and are marketed by Negma in France under the trade name Art 50(R).

Formula-I

Formula II

Diacerein is practically insoluble in solvents such as water, alcohols, acetone, dichloromethane and chloroform, which are generally used in pharmaceutical preparations. Although diacerein can be administered by oral route but it cannot be completely absorbed by the digestive tract, and this incomplete absorption results in undesirable side effects such as soft stools.

In order to overcome these problems, various derivatives, pharmaceutical compositions and specific galenic forms have been proposed in the literature. For example, European patent EP 243,968 describes a diacerein potassium salt, which is water-soluble and can be used in the preparation of compositions for parenteral administration.

Several patents/applications describe pharmaceutical compositions of diacerein. For example, EP243968 describes parenteral preparations of diacerein salts.

U.S. Pat. No. 6,124,358 and European Patent No EP904060 describe pharmaceutical compositions of rhein or diacerein, wherein rhein or diacerein is co-micronized with sodium lauryl sulfate. Although it is possible to improve the bioavailability of diacerein by co-micronization, it is still desirable to develop new formulations or new compositions which are likely to further improve the bioavailability.

U.S. Pat. No. 5,149,542 (EP263083B1); U.S. Pat. No. 4,861,599 (EP 264989B1) and U.S. Pat. No. 5,275,824 (EP 446753B1) describe controlled release or delayed release compositions.

U.S. Pat. No. 5,225,192 (EP 364944B1) and U.S. Pat. No. 5,569,469 describe different poorly soluble medicaments supported on polymer substances.

U.S. Pat. No. 5,952,383 and European Patent No EP 862423B1 provide pharmaceutical compositions of diacerein, rhein and their salts along with excipients.

There are several references known in the literature which disclose use of sugar alcohols like mannitol, sorbitol etc. as fillers in the formulations or as sensory cue agents i.e which impart feeling of cooling in mouth in case of orally disintegrating tablets (WO2007080601, EP589981B1, EP906089B1, EP1109534B1, U.S. Pat. No. 6,328,994, WO2007001086, US20070196494, US20060240101, WO2006057912, US20060057199).

In general, sugar alcohols like mannitol are employed in most orally disintegrating formulations and not in conventional immediate release formulations as sensory cue agents because the orally disintegrating tablets disintegrate in mouth instead of disintegrating in gastrointestinal tract as in the case of conventional immediate release tablets.

The present invention addresses and overcomes these commonly encountered problems of low solubility, incomplete absorption and soft stools.

SUMMARY OF THE INVENTION

In one general aspect there is provided a pharmaceutical composition comprising rhein or diacerein or salts or esters or prodrugs thereof and one or more sugar alcohols.

Embodiments of the pharmaceutical composition may include one or more of the following features. For example, the diacerein may be present in admixture with a sugar alcohol. Alternatively, it may be present in the form of a complex with sugar alcohol or is adsorbed on a sugar alcohol.

The composition may further include one or more pharmaceutically acceptable excipients including fillers, binders, lubricants, sweeteners, coloring and flavoring agents, glidants, disintegrants, surfactants, and the like.

Figure 1:
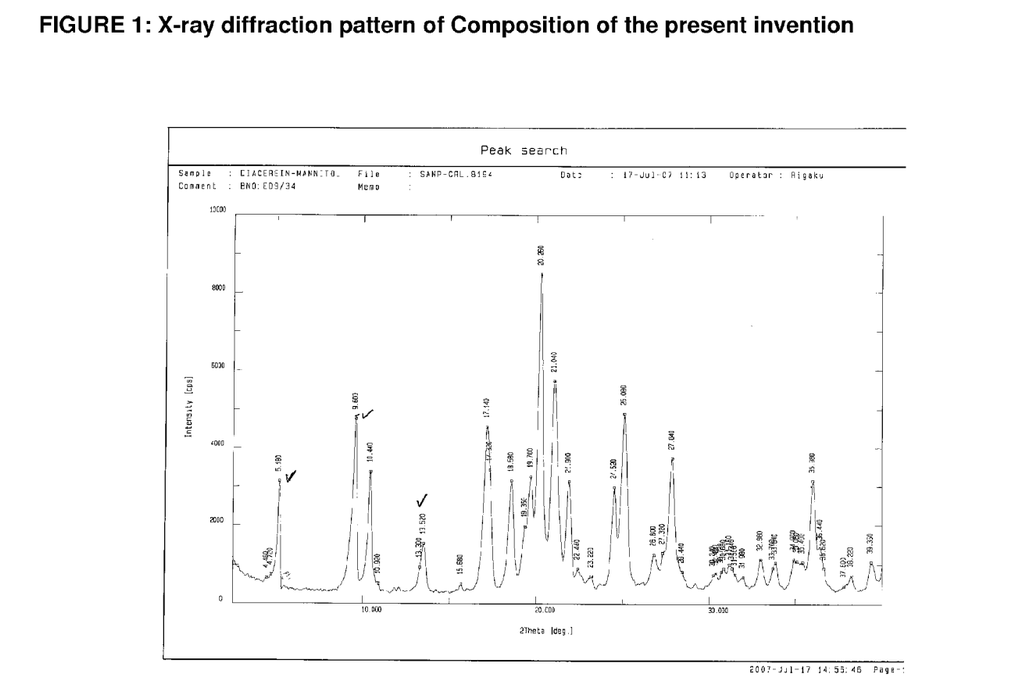
FIG. 1 shows X-ray diffraction pattern of composition of the present invention

In another general aspect there is provided a pharmaceutical composition comprising rhein or diacerein or salts or esters or prodrugs thereof characterized by the crystallographic data shown in FIG. 1.

The composition may have the X-ray diffraction peaks at angle 2 theta of 9.6 and 13.52 degrees.

In another general aspect there is provided a method of improving the solubility of rhein or diacerein or salts or esters or prodrugs thereof, wherein rhein or diacerein or salts or esters or prodrugs thereof is associated with one or more sugar alcohols.

In another general aspect there is provided a process for the preparation of a pharmaceutical composition, the process comprising spraying a solution of rhein or diacerein or salts or esters or prodrugs thereof in one or more organic solvents, optionally with one or more sugar alcohols and/or one or more pharmaceutically acceptable excipients in a flow of a fluid under supercritical pressure to form particles and collecting the particles.

Embodiments of the pharmaceutical composition may include one or more of the following features. For example, the composition may further include one or more pharmaceutically acceptable excipients including fillers, binders, lubricants, sweeteners, coloring and flavoring agents, glidants, disintegrants, surfactants, and the like.

In one general aspect there is provided a pharmaceutical composition comprising rhein or diacerein, or salts or esters or prodrugs thereof adsorbed on a pharmaceutically acceptable adsorbent.

Embodiments of the pharmaceutical composition may include one or more of the following features. For example, the composition may further include one or more pharmaceutically acceptable excipients including fillers, binders, lubricants, sweeteners, coloring and flavoring agents, glidants, disintegrants, surfactants, and the like.

In another general aspect there is provided a process for preparing a pharmaceutical composition comprising rhein or diacerein, or salts or esters or prodrugs thereof, the process comprising:
a) providing a slurry or solution of rhein or diacerein, optionally with one or more pharmaceutically acceptable excipients in one or more suitable solvents;
b) adding pharmaceutically acceptable adsorbent to the slurry or solution of step a) or vice versa; and
c) recovering the rhein or diacerein, or salts thereof adsorbed on a pharmaceutically acceptable adsorbent from the slurry or solution of step b) thereof.

In another general aspect there is provided a pharmaceutical composition comprising rhein or diacerein, or salts or esters or prodrugs thereof and one or more water-soluble cyclodextrins or derivatives thereof.

Embodiments of the pharmaceutical compositions may include one or more of the following features. For example, rhein or diacerein or salts or esters or prodrugs thereof can be present in admixture or a complex form with water-soluble cyclodextrins or derivatives thereof.

The composition may further include one or more pharmaceutically acceptable excipients including fillers, binders, lubricants, sweeteners, coloring and flavoring agents, glidants, disintegrants, surfactants, and the like.

In another general aspect there is provided a process for preparing a pharmaceutical composition comprising rhein or diacerein, or salts or esters or prodrugs thereof thereof, the process comprising:
a) triturating rhein or diacerein with a suitable water soluble cyclodextrin or derivatives thereof optionally with one or more suitable solvents; and
b) mixing the triturate of step a) optionally with one or more pharmaceutically acceptable excipients.

The "pharmaceutical composition" of the present invention as used herein, is meant for oral administration to mammals and refers to tablets, capsules, granules, beads, caplets, disc, pills, sachet, suspension, spheroids, minitablets, granules in a capsule, beads in a capsule, minitablets in a capsule, and the like.

The details of one or more embodiments of the inventions are set forth in the description below. Other features, objects and advantages of the inventions will be apparent from the description and claims.

DETAILED DESCRIPTION OF THE INVENTION

The inventors have discovered that when diacerein is adsorbed on a pharmaceutically acceptable adsorbent that provides large exposed surface area; it results in increased solubility of diacerein which, in turn, leads to a significant increase in percent drug release of diacerein as compared to Art 50(R) (the marketed formulation of diacerein). Art 50(R) releases about 14% of diacerein in 60 minutes, whereas pharmaceutical composition of the invention releases 100% diacerein in 45 minutes. The increased bioavailability further leads to reduction in side effects i.e. soft stools.

The inventors have also discovered that when diacerein is present along with water-soluble cyclodextrins, either as a physical mixture or in the form of any sort of a complex or any other physical or chemical association, it results in a significant increase in the solubility of diacerein and percent drug release of diacerein as compared to Art 50(R) (the marketed formulation of diacerein). Art 50(R) releases about 14% of diacerein in 60 minutes, whereas pharmaceutical composition of the present invention releases 90-100% diacerein in 60 minutes. The increased bioavailability further leads to reduction in side effects i.e. soft stools.

The inventors have further found that sugar alcohols like mannitol or sorbitol when used along with other known water insoluble drugs like fenofibrate, Irbesartan, aripiprazole, entacapone, either as a physical mixture or in the form of a complex does not result in any significant increase in solubility of these poorly soluble drugs. It was also observed that it does not make any significant difference either in solubility or percent release of these poorly soluble drugs, whether these drugs are present alone in the formulation or along with sugar alcohols.

However, the present inventors have discovered that when diacerein is present along with sugar alcohols, either as a physical mixture or in form of any sort of a complex or any other physical or chemical association, it results in a significant increase in the solubility of diacerein and percent drug release of diacerein as compared to Art 50(R) (Marketed formulation of diacerein). Art 50(R) releases about 14% of diacerein in 60 minutes, whereas pharmaceutical composition of the present invention releases about 80-100% diacerein in 60 minutes.

This significant increase in percent release of diacerein is due to dispersion of diacerein in sugar alcohol matrix leading to improved wettability, solubility, and hence increased percent release. This leads to increased bioavailability and reduction in side effects i.e. soft stools.

Figure 2:
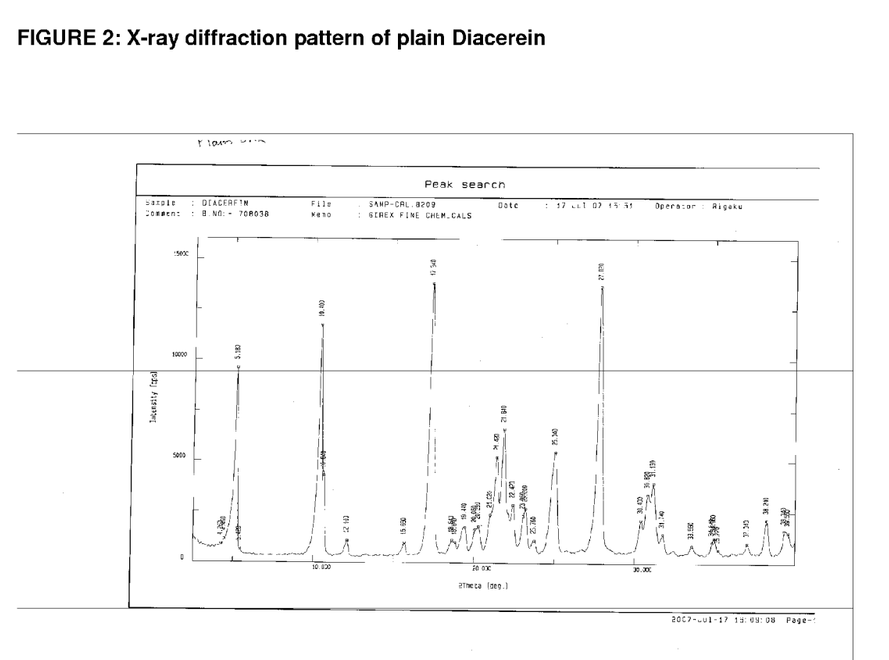
FIG. 2 shows X-ray diffraction pattern of plain diacerein

The inventors have further found that the diacerein-sugar alcohol composition has a different X-ray diffraction pattern as shown in FIG. 1. X-ray diffraction pattern of plain diacerein is shown in FIG. 2. The X-ray spectroscopic analysis of the samples obtained demonstrated the presence of a new crystallographically different entity, as shown in FIG. 1.

The diacerein can be present in an amount relative to the sugar alcohol, such that a molar ratio between the diacerein and the sugar alcohol is from about 1:1 to about 1:10.

The diacerein-sugar alcohol composition can be prepared by various processes including anti-solvent technique, solvent evaporation, kneading, spray drying, colloidal milling, high speed mixing, and trituration.

It was also found that the diacerein-sugar alcohol composition prepared by anti-solvent method using supercritical fluid results in a significant increase in the solubility and percent release of diacerein as compared to composition which contains a mere diacerein-sugar alcohol mixture.

In one embodiment, a pharmaceutical composition can be prepared by spraying a solution of diacerein or salts thereof in one or more organic solvents in a flow of fluid under supercritical pressure to form microparticles, which are collected on a suitable sugar alcohol bed, mixed with other pharmaceutically acceptable excipients and converted into a suitable dosage form.

In another embodiment, a pharmaceutical composition can be prepared by spraying a solution of diacerein or salts thereof in an organic solvent and a suitable sugar alcohol in a flow of fluid under supercritical pressure to form microparticles, which are collected, mixed with other pharmaceutically acceptable excipients and converted into a suitable dosage form.

In yet another embodiment, a pharmaceutical composition can be prepared by triturating diacerein with a sugar alcohol; drying the triturate; mixing the dried triturate with other pharmaceutically acceptable excipients and converting the mixture into a suitable dosage form.

In still another embodiment, a pharmaceutical composition can be prepared by triturating diacerein with a sugar alcohol along with one or more surfactants; drying the triturate; mixing the dried triturate with other pharmaceutically acceptable excipients and converting the mixture into a suitable dosage form.

Suitable fluids which can be used under supercritical pressure may include carbon dioxide, water, ethane, xenon, and the like.

Suitable organic solvents used for preparing organic solution of diacerein or salts thereof are those known to a person of ordinary skill in the art and may include one or more of N-methyl-pyrrolidone, dimethylsulfoxide, dimethylacetamide, tetrahydrofuran, ketones, and the like.

Suitable sugar alcohols may include one or more of mannitol, maltitol, maltol, sorbitol, lactitol, xylitol, and the like.

Suitable surfactants which can be used may include amphoteric, non-ionic, cationic or anionic surfactants. For example, one or more of sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, poloxamer, cremophore RH 40, and the like In yet another embodiment, a pharmaceutical composition can be prepared by dispersing diacerein along with pharmaceutically acceptable excipients in water and adding an adsorbent to diacerein slurry. The mixture thus obtained can be dried, blended with other pharmaceutically acceptable excipients and converted into a suitable dosage form.

In still another embodiment, a pharmaceutical composition can be prepared by dispersing diacerein along with other pharmaceutically acceptable excipients in water and spraying slurry thus obtained on to a pharmaceutically acceptable adsorbent. The mixture thus obtained can be dried, blended with other pharmaceutically acceptable excipients and converted into a suitable dosage form.

Suitable pharmaceutically acceptable adsorbents may include one or more of colloidal silicon dioxide, lactose, saccharides, calcium silicate, magnesium aluminum silicate, porous ceramics, polypropylene foams, cellulose, cellulose derivatives, polyols, starches, pre-gelatinized starches, starch derivatives, modified starches, dextrins, maltodextrins, polydextroses, dextroses, calcium carbonate, calcium phosphate, calcium sulfate, and the like.

The slurry or solution of rhein or diacerein, or salts thereof may be microfluidized through a microfluidizer in order to reduce the particle size of rhein or diacerein.

Suitable solvents which can be used in the process of the present invention include one or more of water, methanol, ethanol, butanol, isopropyl alcohol, acetone, chloroform, dimethyl acetamide (DMA), dimethyl sulfoxide (DMSO), dimethylformamide (DMF), methylene chloride, and the like.

Adsorption may be carried out by a fluidized bed processor, glatt, and spray dryer or by any other suitable coating techniques known in the art.

In general, the rhein or diacerein, or salts thereof adsorbed on a pharmaceutically acceptable adsorbent may be recovered from the suspension by any suitable means, such as removal of the solvent. The removal of the solvent can be carried out by means of drying the mixture with or without vacuum, freeze-drying, or lyophilization, and fluidized bed processor. Drying further includes evaporation and/or distillation or any other means known to a skilled artisan for removal of solvent from a mixture.

In one embodiment, a pharmaceutical composition can be prepared by triturating diacerein with a suitable cyclodextrin with one or more suitable solvents, drying the diacerein-cyclodextrin triturate, mixing the dried triturate optionally with other pharmaceutically acceptable excipients and converting the mixture into a suitable dosage form.

In another embodiment, a pharmaceutical composition of the invention can be prepared by triturating diacerein with a suitable cyclodextrin, mixing the triturate optionally with other pharmaceutically acceptable excipients and converting the mixture into a suitable dosage form.

Suitable water soluble cyclodextrin derivatives may be one or more of, $\beta$-cyclodextrin, $\alpha$-cyclodextrin, $\gamma$-cyclodextrins, hydroxypropyl-$\alpha$-cyclodextrin, hydroxypropyl-$\beta$-cyclodextrin, dimethyl-$\beta$-cylcodextrin, 2-hydroxyethyl-$\beta$-cyclodextrin, trimethyl-$\beta$-cyclodextrin, sulfonated cyclodextrins and the like.

The complex of diacerein and cyclodextrin may be prepared by various processes including anti-solvent technique, solvent evaporation, kneading, spray drying, colloidal milling, high speed mixing, trituration or simple mixing. The diacerein can be present in an amount relative to the cyclodextrin, such that a molar ratio between the diacerein and the cyclodextrin is from about 1:1 to 1:10.

The pharmaceutical compositions can include pharmaceutically acceptable excipients including fillers, binders, lubricants, sweeteners, coloring and flavoring agents, glidants, disintegrants, surfactants, and the like.

Suitable fillers include one or more of microcrystalline cellulose, silicified microcrystalline cellulose, mannitol, calcium phosphate, calcium sulfate, kaolin, dry starch, powdered sugar, and the like.

Suitable binders include one or more of povidone, starch, stearic acid, gums, hydroxypropylmethyl cellulose, and the like.

Suitable surfactants include one or more of sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, poloxamer, cremophore RH 40, and the like.

Suitable lubricants include one or more of magnesium stearate, zinc stearate, calcium stearate, stearic acid, sodium stearyl fumarate, hydrogenated vegetable oil, glyceryl behenate, and the like.

Suitable glidants include one or more of colloidal silicon dioxide, talc or cornstarch, and the like.

Suitable disintegrants include one or more of starch, croscarmellose sodium, crospovidone, sodium starch glycolate, and the like.

The coloring agents of the present invention may be selected from any FDA approved colors for oral use.

The invention is further illustrated by the following examples which are provided merely to be exemplary of the invention and do not limit the scope of the invention. Certain modifications and equivalents will be apparent to those skilled in the art and are intended to be included within the scope of the invention.

The following examples are illustrative of the invention, and are not to be construed as limiting the invention.

EXAMPLE 1

TABLE 1

| S.N. | Ingredients | % w/w |
|---|---|---|
| | Part-I | |
| 1 | Diacerein | 10-60 |
| 2 | Microcrystalline cellulose | 5-70 |
| 3 | Sodium docusate | 1-20 |
| 4 | Sodium lauryl sulfate | 1-20 |
| 5 | Povidone | 5-40 |
| 6 | Water | q.s. |
| | Part-II | |
| 7 | Silicified microcrystalline cellulose | 5-70 |
| 8 | Starch | 10-50 |
| 9 | Croscarmellose sodium | 1-15 |
| 10 | Magnesium stearate | 0.1-3 |

Procedure: Diacerein along with sodium docusate, sodium lauryl sulfate, povidone was dispersed in sufficient quantity of water to get slurry. The slurry was microfluidized through a microfluidizer and the resultant microfluidized slurry was sprayed on microcrystalline cellulose using glatt. The dried mass so obtained was sieved and blended with silicified microcrystalline cellulose, starch, croscarmellose sodium, lubricated with magnesium stearate and the lubricated blend was filled into hard gelatin capsules of a suitable size.

TABLE 2

Dissolution data

| Time (min) | % Drug released (Art 50(R)) | % Drug released (Example-1) |
|---|---|---|
| 5 | 3 | 45 |
| 10 | 4 | 78 |
| 15 | 5 | 89 |
| 20 | 7 | 95 |
| 30 | 9 | 98 |
| 45 | 11 | 100 |
| 60 | 14 | 100 |

Table 2 provides the dissolution data for diacerein capsules prepared as per the formula given in Table 1. For determination of drug release rate, USP Type 2 Apparatus (rpm 75) was used wherein 1000 ml of pH 5.7 phosphate buffer at 37° C.±0.5° C. was used as a medium.

EXAMPLE 2

TABLE 3

| S.N. | Ingredients | % w/w |
|---|---|---|
| | Part-I | |
| 1 | Diacerein | 10-60 |
| 2 | Microcrystalline cellulose | 5-70 |
| 3 | Sodium docusate | 1-20 |
| 4 | Sodium lauryl sulfate | 1-20 |
| 5 | Povidone | 5-40 |
| 6 | Water | q.s. |
| | Part-II | |
| 7 | Silicified microcrystalline cellulose | 5-70 |
| 8 | Starch | 10-50 |
| 9 | Croscarmellose sodium | 1-15 |
| 10 | Magnesium stearate | 0.1-3 |

Procedure: Diacerein along with sodium docusate, sodium lauryl sulfate, povidone was dispersed in a sufficient quantity of water to get slurry. Microcrystalline cellulose was added to the slurry under stirring. The wet mass thus obtained was tray dried overnight in an oven at 35-40° C. The dried mass was sieved and blended with silicified microcrystalline cellulose, starch, croscarmellose sodium, lubricated with magnesium stearate and the lubricated blend was filled into hard gelatin capsules of a suitable size.

EXAMPLE 3

TABLE 4

| S.N. | Ingredients | Qty/Caps (% w/w) |
|---|---|---|
| 1 | Diacerein | 10-90 |
| 2 | Hydroxy propyl beta cyclodextrin | 20-65 |
| 3 | Purified water | q.s. |
| 4 | Sorbitol | 0.5-20 |
| 5 | Crospovidone | 5-40 |
| 6 | Silicified microcrystalline cellulose | 15-50 |
| 7 | Sodium stearyl fumarate | 0.5-2 |

Procedure: Diacerein and hydroxypropyl beta cyclodextrin were mixed and triturated with water for few minutes. Diacerein hydroxypropyl cyclodextrin complex thus formed was dried, sized to a suitable size and mixed with sorbitol, crospovidone, silicified microcrystalline cellulose and sodium stearyl fumarate. The final mixture was filled into hard gelatin capsules of a suitable size.

TABLE 5

Dissolution data

| Time (min) | % Drug released (Art 50(R)) | % Drug released (Example-3) |
|---|---|---|
| 5 | 3 | 39 |
| 10 | 4 | 69 |
| 15 | 5 | 81 |
| 20 | 7 | 87 |
| 30 | 9 | 91 |
| 45 | 11 | 93 |
| 60 | 14 | 96 |

Table 5 provides the dissolution data for diacerein capsules prepared as per the formula given in Table 4. For determination of drug release rate, USP Type 2 Apparatus (rpm 75) was used wherein 1000 ml of pH 5.7 Tampon phosphate buffer at 37° C.±0.5° C. was used as a medium.

EXAMPLE 4

TABLE 6

| S.N. | Ingredients | Qty/Caps (% w/w) |
|---|---|---|
| 1 | Diacerein | 10-90 |
| 2 | Hydroxy propyl beta cylodextrin | 20-65 |
| 3 | Purified water:isopropyl alcohol | q.s. |
| 4 | Sorbitol | 0.5-20 |
| 5 | Crospovidone | 5-40 |
| 6 | Silicified microcrystalline cellulose | 15-50 |
| 7 | Sodium stearyl fumarate | 0.5-2 |

Procedure: Diacerein and hydroxypropyl beta cyclodextrin were mixed and triturated with water/isopropyl mixture for few minutes. The diacerein hydroxypropyl cyclodextrin complex thus formed was dried, sized to a suitable size and mixed with sorbitol, crospovidone, silicified microcrystalline cellulose and sodium stearyl fumarate. The final mixture was filled into hard gelatin capsules of a suitable size.

TABLE 7

| Dissolution data | | |
|---|---|---|
| Time (min) | % Drug released (Art 50(R)) | % Drug released (Example-4) |
| 5 | 3 | 33 |
| 10 | 4 | 62 |
| 15 | 5 | 73 |
| 20 | 7 | 79 |
| 30 | 9 | 83 |
| 45 | 11 | 90 |
| 60 | 14 | 94 |

Table 7 provides the dissolution data for diacerein capsules (50 mg) prepared as per the formula given in Table 6. For determination of drug release rate, USP Type 2 Apparatus (rpm 75) was used wherein 1000 ml of pH 5.7 Tampon phosphate buffer at 37° C.±0.5° C. was used as a medium.

EXAMPLE 5

TABLE 8

| S.N. | Ingredients | Qty/Caps (% w/w) |
|---|---|---|
| 1 | Diacerein | 10-90 |
| 2 | Hydroxy propyl beta cyclodextrin | 20-65 |
| 3 | Sorbitol | 0.5-20 |
| 4 | Crospovidone | 5-40 |
| 5 | Silicified microcrystalline cellulose | 15-50 |
| 6 | Sodium stearyl fumarate | 0.5-2 |

Procedure: Diacerein and hydroxypropyl beta cyclodextrin were mixed and triturated for few minutes. The diacerein hydroxypropyl cyclodextrin complex thus formed was mixed with sorbitol, crospovidone, silicified microcrystalline cellulose and sodium stearyl fumarate. The final mixture was filled in to hard gelatin capsules of a suitable size.

EXAMPLE 6

TABLE 9

| S.N. | Ingredients | Qty/Tabs (% w/w) |
|---|---|---|
| 1 | Diacerein | 10-90 |
| 2 | Hydroxy propyl beta cyclodextrin | 20-65 |
| 3 | Purified water | q.s. |
| 4 | Sorbitol | 0.5-20 |
| 5 | Crospovidone | 5-40 |
| 6 | Silicified microcrystalline cellulose | 15-50 |
| 7 | Sodium stearyl fumarate | 0.5-2 |

Procedure: Diacerein and hydroxypropyl beta cyclodextrin were mixed and triturated with water for few minutes. The diacerein hydroxypropyl cyclodextrin complex thus formed was dried, sized to a suitable size and mixed with sorbitol, crospovidone, silicified microcrystalline cellulose and sodium stearyl fumarate. The final mixture was compressed into tablets using a suitable tooling.

TABLE 10

| Dissolution data | | |
|---|---|---|
| Time (min) | % drug released (Art 50(R)) | % drug released (Example-6) |
| 5 | 3 | 62 |
| 10 | 4 | 78 |
| 15 | 5 | 85 |
| 20 | 7 | 88 |
| 30 | 9 | 91 |
| 45 | 11 | 94 |
| 60 | 14 | 98 |

Table 10 provides the dissolution data for diacerein capsules (50 mg) prepared as per the formula given in Table 9. For determination of drug release rate, USP Type 2 Apparatus (rpm 75) was used wherein 1000 ml of pH 5.7 Tampon phosphate buffer at 37° C.±0.5° C. was used as a medium.

EXAMPLE 7

TABLE 11

| S.N. | Ingredients | % w/w |
|---|---|---|
| Part I | | |
| 1 | Diacerein | 10-90 |
| 2 | Sorbitol | 0.5-20 |
| Part II | | |
| 3 | Microcrystalline cellulose | 5-60 |
| 4 | Croscarmellose sodium | 1-25 |
| 5 | Magnesium stearate | 1-15 |

Procedure: Diacerein was mixed with sorbitol and triturated with minimum amount of water to form a pasty mass. The pasty mass was dried, sieved to form granules and mixed with microcrystalline cellulose, croscarmellose sodium, and magnesium stearate. The final mixture was filled into hard gelatin capsules.

TABLE 12

Dissolution data

| Time (min) | % Drug released (ART 50(R)) | % Drug released (Example-7) |
|---|---|---|
| 5 | 3 | 29 |
| 10 | 4 | 53 |
| 15 | 5 | 68 |
| 20 | 7 | 76 |
| 30 | 9 | 82 |
| 45 | 11 | 89 |
| 60 | 14 | 90 |

Table 12 provides the dissolution data for diacerein capsules (50 mg) prepared as per the formula given in Table 11. For determination of drug release rate, USP Type 2 Apparatus (rpm 75) was used wherein 1000 ml of pH 5.7 phosphate buffer at 37° C.±0.5° C. was used as a medium.

EXAMPLE 8

TABLE 13

| S.N. | Ingredients | % w/w |
|---|---|---|
| | Part I | |
| 1 | Diacerein | 10-60 |
| 2 | Sorbitol | 0.5-20 |
| 3 | Docusate sodium | 1-20 |
| 4 | Sodium lauryl sulfate | 1-20 |
| | Part II | |
| 5 | Glycine | 1-20 |
| 6 | Lactose | 5-40 |
| 7 | Crospovidone | 5-40 |

Procedure: Diacerein was mixed with sorbitol, sodium docusate, sodium lauryl sulfate and triturated with minimum amount of water to form a pasty mass. The pasty mass was dried, sieved to form granules and mixed with glycine, lactose and crospovidone. The final mixture was filled into hard gelatin capsules.

TABLE 14

Dissolution data

| Time (min) | % Drug released (Art 50) | % Drug released (Example-8) |
|---|---|---|
| 5 | 3 | 16 |
| 10 | 4 | 35 |
| 15 | 5 | 50 |
| 20 | 7 | 60 |
| 30 | 9 | 72 |
| 45 | 11 | 78 |
| 60 | 14 | 82 |

Table 14 provides the dissolution data for diacerein capsules (50 mg) prepared as per the formula given in Table 13. For determination of drug release rate, USP Type 2 Apparatus (rpm 75) was used wherein 1000 ml of pH 5.7 phosphate buffer at 37° C.±0.5° C. was used as a medium.

EXAMPLE 9

TABLE 15

| S.N. | Ingredients | % w/w |
|---|---|---|
| | Part I | |
| 1 | Diacerein | 10-90 |
| 2 | N-methyl pyrrolidone | qs |
| 3 | Mannitol | 10-90 |
| | Part II | |
| 4 | Microcrystalline cellulose | 5-60 |
| 5 | Croscarmellose sodium | 1-25 |
| 6 | Magnesium stearate | 1-15 |

Procedure: Diacerein was dissolved in N-methylpyrrolidone and sprayed (Spray rate: 3 ml/min) in a flow of carbon dioxide (15 Kg/h) under supercritical pressure (100 bars, 40° C.) on bed of mannitol placed in a spray reactor. The particles thus formed were recovered on the bed of mannitol and mixed with microcrystalline cellulose, croscarmellose sodium, and magnesium stearate. The final mixture was filled into hard gelatin capsules.

TABLE 16

Dissolution data

| Time (min) | % Drug released (ART 50(R)) | % Drug released (Example-9) |
|---|---|---|
| 5 | 3 | 27 |
| 10 | 4 | 45 |
| 15 | 5 | 60 |
| 20 | 7 | 69 |
| 30 | 9 | 82 |
| 45 | 11 | 88 |
| 60 | 14 | 95 |

Table 16 provides the dissolution data for diacerein capsules (50 mg) prepared as per the formula given in Table 15. For determination of drug release rate, USP Type 2 Apparatus (rpm 75) was used wherein 1000 ml of pH 5.7 phosphate buffer at 37° C.±0.5° C. was used as a medium.

EXAMPLE-10

TABLE 17

| S.N. | Ingredients | % w/w |
|---|---|---|
| | Part I | |
| 1 | Diacerein | 10-90 |
| 2 | Mannitol | 10-90 |
| 3 | N-methyl pyrrolidone | qs |
| | Part II | |
| 3 | Microcrystalline cellulose | 5-60 |
| 4 | Croscarmellose sodium | 1-25 |
| 5 | Magnesium stearate | 1-15 |

Procedure: Diacerein and mannitol were dissolved in N-methylpyrrolidone and sprayed (Spray rate: 3 ml/min) in a flow of carbon dioxide (15 Kg/h) under supercritical pressure (100 bars, 40° C.) in a spray reactor. The particles thus formed were recovered and mixed with microcrystalline cellulose, croscarmellose sodium, and magnesium stearate. The final mixture was filled into hard gelatin capsules.

TABLE 18

Dissolution data

| Time (min) | % Drug released (Art 50(R)) | % Drug released (Example-10) |
|---|---|---|
| 5 | 3 | 92 |
| 10 | 4 | 100 |
| 15 | 5 | 100 |
| 20 | 7 | 100 |
| 30 | 9 | 100 |
| 45 | 11 | 100 |
| 60 | 14 | 100 |

Figure 3:
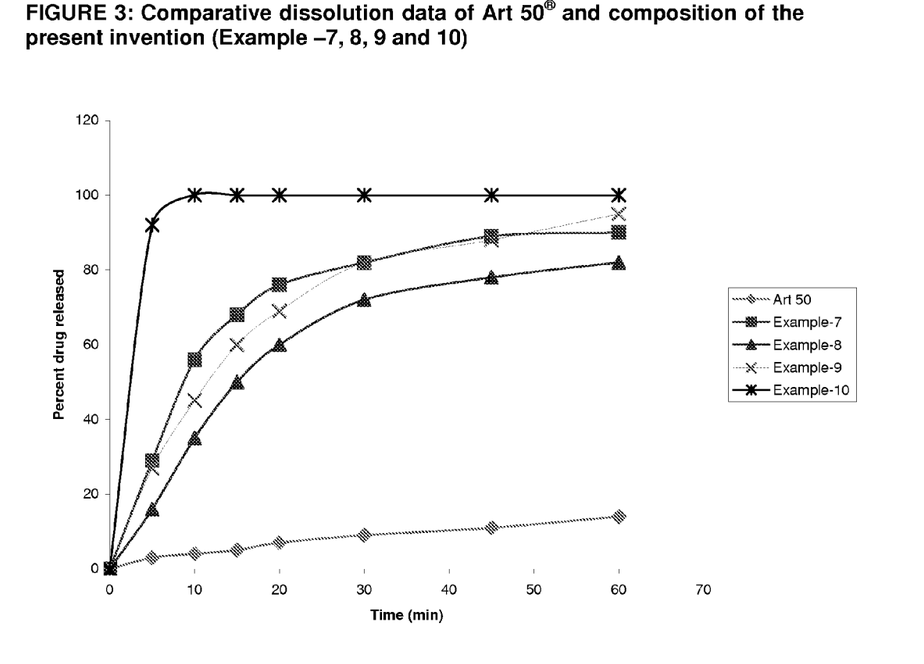
FIG. 3 shows comparative dissolution data of Art 50(R) and composition of the present invention (Examples 7, 8, 9 and 10)

Table 18 provides the dissolution data for diacerein capsules prepared as per the formula given in Table 17. For determination of drug release rate, USP Type 2 Apparatus (rpm 75) was used wherein 1000 ml of pH 5.7 phosphate buffer at 37° C.±0.5° C. was used as medium. Comparative dissolution profile of Art 50(R), Example 7, 8, 9 and 10 is shown in FIG. 3.

While the invention has been described in terms of its specific embodiments, certain modifications and equivalents will be apparent to those skilled in the art and are intended to be included within the scope of the invention.

The invention claimed is:

1. A pharmaceutical composition comprising a slurry or solution of diacerein adsorbed on a pharmaceutically acceptable adsorbent, wherein the composition exhibits a dissolution profile such that more than 85% of diacerein is released within 20 minutes, wherein the release rate is measured in Apparatus 2 USP, Dissolution, paddle, 75 rpm using 1000 ml of pH 5.7 phosphate buffer at 37° C.±0.5° C., wherein the pharmaceutical composition comprises the following ingredients:

| Ingredients | % w/w |
|---|---|
| Part-I | |
| Diacerein | 10-60 |
| Microcrystalline cellulose | 5-70 |
| Sodium docusate | 1-20 |
| Sodium lauryl sulfate | 1-20 |
| Povidone | 5-40 |
| Water | q.s. |
| Part-II | |
| Silicified microcrystalline cellulose | 5-70 |
| Starch | 10-50 |
| Croscarmellose sodium | 1-15 |
| Magnesium stearate | 0.1-3 |

2. A pharmaceutical composition comprising a slurry or solution of diacerein adsorbed on a pharmaceutically acceptable adsorbent, wherein the composition exhibits a dissolution profile such that more than 85% of diacerein is released within 20 minutes, wherein the release rate is measured in Apparatus 2 USP, Dissolution, paddle, 75 rpm using 1000 ml of pH 5.7 phosphate buffer at 37° C.±0.5° C., wherein the pharmaceutical composition comprises the following ingredients:

| Ingredients | Qty/Caps (% w/w) |
|---|---|
| Diacerein | 10-90 |
| Hydroxy propyl beta cyclodextrin | 20-65 |
| Purified water | q.s. |
| Sorbitol | 0.5-20 |
| Crospovidone | 5-40 |
| Silicified microcrystalline cellulose | 15-50 |
| Sodium stearyl fumarate | 0.5-2 |

3. A pharmaceutical composition comprising a pasty mass of diacerein adsorbed on a pharmaceutically acceptable adsorbent, wherein the composition exhibits a dissolution profile such that more than 85% of diacerein is released within 45 minutes, wherein the release rate is measured in Apparatus 2 USP, Dissolution, paddle, 75 rpm using 1000 ml of pH 5.7 phosphate buffer at 37° C.±0.5° C., wherein the pharmaceutical composition comprises water and wherein the pharmaceutical composition comprises the following ingredients:

| Ingredients | % w/w |
|---|---|
| Part I | |
| Diacerein | 10-90 |
| Sorbitol | 0.5-20 |
| Part II | |
| Microcrystalline cellulose | 5-60 |
| Croscarmellose sodium | 1-25 |
| Magnesium stearate | 1-15 |

4. A pharmaceutical composition comprising a pasty mass of diacerein adsorbed on a pharmaceutically acceptable adsorbent, wherein the composition exhibits a dissolution profile such that more than 50% of diacerein is released within 20 minutes, wherein the release rate is measured in Apparatus 2 USP, Dissolution, paddle, 75 rpm using 1000 ml of pH 5.7 phosphate buffer at 37° C.±0.5° C., wherein the pharmaceutical composition comprises water and wherein the pharmaceutical composition comprises the following ingredients:

| Ingredients | % w/w |
|---|---|
| Part I | |
| Diacerein | 10-60 |
| Sorbitol | 0.5-20 |
| Docusate sodium | 1-20 |
| Sodium lauryl sulfate | 1-20 |
| Part II | |
| Glycine | 1-20 |
| Lactose | 5-40 |
| Crospovidone | 5-40 |

5. A pharmaceutical composition comprising diacerein dissolved in N-methylpyrrolidone and adsorbed on a pharmaceutically acceptable adsorbent, wherein the composition exhibits a dissolution profile such that more than 60% of diacerein is released within 20 minutes, wherein the release rate is measured in Apparatus 2 USP, Dissolution, paddle, 75 rpm using 1000 ml of pH 5.7 phosphate buffer at 37° C.±0.5° C., wherein the pharmaceutical composition comprises the following ingredients:

| Ingredients | % w/w |
|---|---|
| Part I | |
| Diacerein | 10-90 |
| N-methyl pyrrolidone | qs |
| Mannitol | 10-90 |
| Part II | |
| Microcrystalline cellulose | 5-60 |
| Croscarmellose sodium | 1-25 |
| Magnesium stearate | 1-15 |

6. A process for preparing a pharmaceutical composition as claimed in any of claims 1-5, wherein the process comprises: (a) providing a slurry, solution, or pasty mass of diacerein, optionally with one or more pharmaceutically acceptable excipients in one or more suitable solvents; (b) adding pharmaceutically acceptable adsorbent to the slurry, solution, or pasty mass of step a) or vice versa; and (c) recovering the diacerein adsorbed on the pharmaceutically acceptable adsorbent from the slurry, solution, or pasty mass of step b) thereof; wherein the suitable solvent comprises one or more of water, methanol, ethanol, butanol, isopropyl alcohol, acetone, chloroform, dimethylacetamide, di methylsulfoxide, dimethylformamide and methylene chloride.

* * * * *